US00H002258H

(19) United States
(12) Statutory Invention Registration
Arnevik et al.

(10) Reg. No.: US H2258 H
(43) Published: Jun. 7, 2011

(54) DEVELOPMENT OF NOVEL GERMPLASM USING SEGREGATES FROM TRANSGENIC CROSSES

(75) Inventors: Cindy L. Arnevik, Troy, MO (US); Raymond Dobert, O'Fallon, MO (US); Qingyi Zeng, Chesterfield, MO (US); Jennifer Listello, O'Fallon, MO (US); Gregory R. Heck, Crystal Lake Park, MO (US); John Soteres, Olivette, MO (US); Kunsheng Wu, Ballwin, MO (US)

(73) Assignee: Monsanto Technology LLC, St. Louis, MO (US)

(21) Appl. No.: 11/490,708

(22) Filed: Jul. 21, 2006

(65) Prior Publication Data

US 2007/0136836 A1 Jun. 14, 2007

Related U.S. Application Data

(60) Provisional application No. 60/703,917, filed on Jul. 29, 2005.

(51) Int. Cl.

| | |
|---|---|
| ***A01H 5/00*** | (2006.01) |
| ***C12N 15/82*** | (2006.01) |
| ***C12N 5/04*** | (2006.01) |

(52) U.S. Cl. ..... 800/278; 800/312; 435/468; 435/415

(58) Field of Classification Search ..... None
See application file for complete search history.

(56) References Cited

U.S. PATENT DOCUMENTS

| | | | | |
|---|---|---|---|---|
| 5,792,924 | A | 8/1998 | Yoder et al. | 800/205 |
| 6,040,497 | A | 3/2000 | Spencer et al. | |
| 6,353,026 | B1 | 3/2002 | Serhan | |
| 6,468,747 | B1 | 10/2002 | De Beuckeleer et al. | |
| 6,740,488 | B2 | 5/2004 | Rangwala et al. | 435/6 |
| 6,818,807 | B2 | 11/2004 | Trolinder et al. | |
| 6,825,400 | B2 | 11/2004 | Behr et al. | |
| 6,927,319 | B2 * | 8/2005 | Davis | 800/266 |
| 2003/0024005 | A1 * | 1/2003 | Hillyard et al. | 800/278 |
| 2005/0132437 | A1 | 6/2005 | Dizigan et al. | 800/278 |
| 2007/0136836 | A1 * | 6/2007 | Arnevik et al. | 800/278 |

FOREIGN PATENT DOCUMENTS

| | | |
|---|---|---|
| WO | WO 92/01370 | 2/1992 |
| WO | WO 03/003816 A2 | 1/2003 |
| WO | WO 03/064696 A2 | 8/2003 |

OTHER PUBLICATIONS

Spencer et al 1992, Plant Molecular Biology 18: 201–210.*

Lopez et al, Presentation at the Xth EAAE Congress Exploring Diversity in the European Agri–Food System, Zaragoza (Spain), 28031 Aug. 2002, 13 pages plus cover page.*

Honda et al 2002, J. Exp. Bot. 53: 1515–1520.*

(Continued)

*Primary Examiner*—Dan Pihulic
(74) *Attorney, Agent, or Firm*—Pamela J. Sisson

(57) ABSTRACT

This invention provides a method for the development of novel plant germplasm using segregates from a transgenic line combined with PCR-based zygosity testing and, optionally, Southern blot analysis.

30 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

OTHER PUBLICATIONS

Berdal et al 2001, Eur. Food Res. Techol. 213: 432–438.*

Ben Bubner et al., "Use of Real–Time PCR for Determing Copy Number and Zygosity in Transgenic Plants," *Plant Cell Rep.*, 23:263–271 (2004).

Pieter Windels et al., "Characterisation of the Roundup Ready Soybean Insert," *Eur. Food Res. Technol.*, 213:107–112 (2001).

Peter D. Hare et al., "Excision of Selectable Marker Genes from Transgenic Plants," *Nature Biotechnology*, 20:575–580 (2002).

Ben Bubner et al., "Two–Fold Differences are the Detection Limit for Determing Transgene Copy Numbers in Plants by Real–Time PCR," *BMC Biotechnology*, 4:14 (2004).

P. Song et al., "Quantitative Real–Time PCR as a Screening Tool for Estimating Transgene Copy Number in WHISKERS™–Derived Transgenic Maize," *Plant Cell Rep.*, 20:948–954 (2002).

M.A. Schmidt et al., "Quantitative Detection of Transgenes in Soybean [*Glycine max* ( L.) Merrill] and Peanut (*Arachis hypogaea* L.) by Real–Time Polymerase Chain Reaction," *Plant Cell Rep.*, 20:422–428 (2001).

S.R. Padgette et al., "Development, Identification, and Characterization of Glyphosate–Tolerant Soybean Line," *Crop Sci.*, 35:1451–1461 (1995).

P. Windels et al., "Development of a Line Specific GMO Detection Method: A Case Study," *Med. Fac. Landbouww*, XP–001032975, (1999).

Taverniers, Isabel et al., "Event–Specific Plasmid Standards and Real–Time PCR Methods for Transgenic Bt11, Bt176, and GA21 Maize and Transgenic GT73 Canola," 2005, *Journal of Agricultural and Food Chemistry*, vol. 53, No. 8, pp. 3041–3052, (XP002422926).

Hernández, Marta et al., "Development of real–time PCR systems based on SYBR® Green I, Amplifluor™ and Tagman ® technologies for specific quantitative detection of the transgenic maize event GA21," 2004, *Journal of Cereal Science*, vol. 39, No. 1, pp. 99–107, (XP–002422925).

"DNA Sequences Flanking the 3' End of the Functional Insert of Roundup Ready Soybean Event 40–3–2 are Identical to DNA Sequences from the Wild–type Soybean Lines A5403 and A3244," 2002, *Report No. MSL–17561*, [www.food.gov.uk/multimedia/pdfs/soygenome_clean_MSL17561.pdf] pp. 1–7, (XP002422924).

"Updated Molecular Characterization and Safety Assessment of Roundup Ready® Soybean Event 40–3–2," 2000, *Monsanto Report MSL–16712*, [www.agbios.com/docroot/decdocs/gts40–3–3–update.pdf] pp. 1–20, (XP–002422923).

Monsanto Company Study #: 99–01–30–22, *Report MSL–16646*, [www.food.gov.uk/multimedia/pdfs/monsantodossier.pdf] pp. 1–47, (XP002422922).

Terry, Catherine F et al., "Event–specific detection of Roundup Ready Soya using two different real time PCR detection chemistries," 2001, *European Food Research and Technology*, vol. 213, No. 6, pp. 425–431, (XP–001097295).

Taverniers, Isabel et al., "Use of cloned DNA fragments for event–specific quantification of genetically modified organisms in pure and mixed food products," 2001, *European Food Research and Technology*, vol. 213, No. 6, pp. 417–424, (XP008072736).

Berdal, Knut et al., "Roundup Ready® soybean event–specific real–time quantitive PCR assay and estimation of the practical detection and quantification limits in GMO analyses," 2001, *European Food Research and Technology*, vol. 213, No. 6, pp. 432–438, (XP001097294).

Office Action regarding Argentine Application No. P20060113316, dated Apr. 13, 2010.

* cited by examiner

DEVELOPMENT OF NOVEL GERMPLASM USING SEGREGATES FROM TRANSGENIC CROSSES

This application claims benefit of U.S. Provisional application Ser. No. 60/703,917 filed Jul. 29, 2005, the entire contents of which are incorporated by reference herein.

FIELD OF THE INVENTION

The invention in the field of plant breeding provides a method for the development of plant germplasm using segregates from a transgenic line. A method of zygosity testing to evaluate for the absence of a transgene is also disclosed.

BACKGROUND OF THE INVENTION

Widely planted crop germplasm often represents the most elite lines containing a combination of the yield, agronomic, and pest and disease resistance traits most desired by growers. Because of its combination of elite traits, this germplasm may serve to generate commercially available seed, and may also be used as a source or future plant breeding efforts. In some cases, this germplasm may often comprise a transgenic trait in addition to the elite traits it exhibits. Thus, there exists a need in the field of plant breeding for methods to use the full complement of the existing germplasm base of a crop in plant breeding, regardless of whether a transgene is present in any of the elite varieties that might be used for breeding experiments. Methods to further apply zygosity testing to improve the efficiency of plant breeding efforts are also needed.

Zygosity and copy-number testing based on real-time quantitative TAQMAN™ PCR (qRT-PCR) has been used to analyze transgenic plant progeny (e.g. Bubner and Baldwin, Plant Cell Rep. 23:263-271(2004)). This technique can allow detection and quantization of the copy number of a given DNA sequence in a plant genome, and requires only a small amount of plant tissue. The technique is much less labor intensive per sample the previously employed methods, such as Southern blotting, for detecting and quantitating transgene copy numbers. Nevertheless, it is notoriously sensitive to the concentration and purity of the starting template DNA, among other variables. As such, its use has been primarily as a first screen for the copy number of a transgene before selective breading is begun in earnest, with subsequent confirmation of results by other means such as Southern blotting. It is known to be suited, for instance, for identifying high copy number events that may be discarded early in a oxygenic plant event analysis prior to selected events being passed on to breeders. The method has not been used with single copy elite transgenic breeding material.

If a transgenic plant line is to be used in a breeding program, efficient methods for removing a transgene, or screening for its loss are desirable. Specific removal of transgene sequences, such as a gene encoding a selectable marker, has been reported, including the Cre/lox recombinase system (Hare and Chua Nature Biotechnol. 20:575-580 (2002)). This method can specifically lead to removal of inserted transgenic DNA sequences from a transgenic plant, but lox site sequences necessarily still remain, flanking the site of the excised sequence. Screening for loss of a transgene by genetic segregation in progeny is another method that is widely known but requires substantial time and effort to achieve. Thus, more efficient methods to screen for loss of specific sequences are desirable, especially methods that ensure the complete removal of all inserted transgenic sequences.

A significant portion of recent soybean breeding has utilized lines containing the ROUNDUP READY® trait found in event 40-3-2, because possibly as much as 80-95% of the soybean germplasm offered for sale in the United States currently contains this transgenic event. This germplasm exhibits a set of agronomic traits superior to the non-transgenic A5403 parent line, and to many conventional (i.e. non-transgenic) soybean breeding lines. Thus these transgenic ROUNDUP READY® soybean varieties are themselves useful in plant breeding programs. In order to fully realize their usefulness, it is desirable to be able to identify progeny of these ROUNDUP READY® lines that retain the elite agronomic traits of the parental line except for glyphosate resistance derived from the transgene insert of event 40-3-2 and the associated transgenic sequences found in event 40-3-2.

The sequences of the functional transgene of soybean event 40-3-2 and its associated flanking plant DNA can be used to detect the presence of the transgene in progeny of 40-3-2. The DNA sequence flanking the functional transgenic insert in soybean event 40-3-2 has been characterized (Padgette et al. Crop Sci. 35:1451-1461 (1995); Windels et al. Eur. Food Res. Technol. 213:107-112(2001).

Regulatory approval in many countries for release and commercialization of a particular transgenic plant event may require disclosure of genomic DNA sequences flanking an inserted DNA, and a method to detect DNA specific or the event. Accordingly, some sequences flanking the functional insertion in soybean event 40-3-2 have been reported previously (Monsanto MSL-16646, available at http link for //archive.food.gov.uk/pdf_files/acnfp/dossier.pdf). A method of detection for corn comprising transgenic event NK603 has also been reported at http link //gmo-crl.jrc.it/detectionmethods.htm.

SUMMARY OF THE INVENTION

Plant breeders may utilize a set of "elite" cultivars exhibiting superior traits related to growth, adaptability, pest and disease resistance, seed yield, lodging resistance, emergence, maturity, late season plant intactness, plant height and shattering resistance among others, as a basis to develop new improved crop cultivars. These packages of traits can then be introduced into new breeding lines with one or more additional desired traits in order to efficiently improve the breeding germplasm. If the elite cultivar that is being used as a basis for further breeding already comprises a transgene, it is useful to be able to identify the presence or absence of the transgene among many segregating progeny while these progeny are being screened by classical plant breeding methods for their other agronomy qualities.

Plant breeders practicing the invention may use various techniques. Recurrent selection is a breeding procedure designed to accumulate favorable genes for a trait or traits in a population. Parent lines are crossed, their progeny are evaluated for one or more traits, and the progenies which best express the trait are intercrossed to repeat the process over successive generations. Variations on recurrent selection include, among others, full-sib selection, half-sib family selection, and $S_1$ progeny recurrent selection. Techniques such as backcross breeding, mass selection, and marker-assisted breeding may also be employed. These techniques may be used to select for traits of interest in self-pollinated and cross-pollinated crops, as appropriate.

This invention relates to, in part, a method for developing an elite crop variety, comprising crossing a first elite line exhibiting a useful trait and comprising a transgene that encodes the useful trait, and which exhibits additional elite traits or characteristics, with a second line that exhibits a useful trait; obtaining individual F1 hybrid lines; selecting at least one F1 hybrid individual that exhibits a useful trait from the first or second line; deriving at least one further progeny generation of seeds or plants from the selected F1 hybrid individual; screening F2 or later progeny exhibiting at least one of the additional elite traits or characteristics of the first line for the presence of the transgene; and identifying at least one individual lacking the transgene, wherein the useful trait is derived from the second line.

In another aspect of the invention is a method of determining the zygosity of the hybrid progeny comprising: (a) contacting a sample comprising DNA derived from the progeny with a primer set comprising SEQ ID NO:3, SEQ ID NO:4 and SEQ ID NO:6, that when used in a nucleic-acid amplification reaction with genomic DNA from the progeny, produces a first amplicon that is diagnostic for the trangenic event; and (b) performing a nucleic acid amplification reaction, thereby producing the first amplicon; and (c) detecting the first amplicon; and (d) contacting the sample comprising progeny DNA with a primer set comprising SEQ ID NOs: 4, 5, and 7, that when used in a nucleic-acid amplification reaction with genomic DNA from progeny plants produces a second amplicon comprising the native genomic DNA homologous to the genomic region in which the transgene is inserted; and (e) performing a nucleic acid amplification reaction, thereby producing the second amplicon; and (f) detecting the second amplicon; and (g) comparing the first and second amplicons in a sample, wherein the presence of both amplicons indicates the sample is heterozygous for the transgene insertion.

In particular, the introduction of a new transgenic glyphosate tolerant trait into a soybean line already comprising event 40-3-2 would require the ability to distinguish between two events, since the application of glyphosate selection would not serve to identify the presence of the new event from the previous one. Additionally, if the new event comprises the same functional transgene as a previous event, ELISA technology would also be unable to distinguish the presence of either or both events. ELISA or other protein detection methods could allow a breeder to identify the presence of a novel glyphosate resistance trait in a line lacking any other copy of the transgene, but would not allow a breeder to evaluate in a positive manner whether any genetic elements attributed to event 40-3-2 still remain.

For evaluating and breeding traits that confer glyphosate tolerance either by themselves, or in vector stacks with other traits of value to producers, the use of DNA technology, in particular PCR zygosity technology based on flanking sequences for the 40-3-2 event will increase the efficiency of the selection process, and a breeder's ability to build upon the existing germplasm base that already contains event 40-3-2 as well as other useful traits. This is currently the only method that can demonstrate the absence of all identified genetic elements of the 40-3-2 event in breeding populations in a relatively inexpensive manner.

Corn breeding, for instance encompassing conversion of a corn line comprising a first event such as GA21 to a second event such as one comprising NK603, is also a subject of the present invention. Identification of a GA21-null segregant line that comprises event NK603 and lacks the presence of sequences associated with the GA21 event, following a cross between transgenic corn lines comprising events GA21 and NK603, is also a subject of the present invention.

In accordance with an aspect of the invention, mutagenesis can be used to create viable reproducible soybeans or other species of plant with unique genetic profiles string with transgenic lines from which the transgene is to be removed. For example, mutagenesis of transgenic soybean or other species can be induced by treatment with a variety of mutagenic agents known in the art, including physical mutagens such as X-rays, gamma rays, fast or thermal neutrons, protons, and chemical mutagens such as ethyl methanesulfonate (EMS), diethyl sulfate (DES), ethyleneimine (EI), propane sultane, N-methyl-N-nitrosourethane (MNW, N-nitroso-N-methylurea (NMU), N-ethyl-N-nitrosourea (ENU) and sodium azide. For examples of these methods see Ohshima et al. (1998) Virology 243: 472-481; Okubara et al. (1994) Genetics 137: 867-874; Quesada et al. (2000) Genetics 154: 421-436. In addition, a fast and automatable method for screening for chemically induced mutations, TILLING (Targeting Induced Local Lesions In Genomes), using a denaturing HPLC or selective endonuclease digestion of selected PCR products is also applicable to the instant invention (see McCallum et al. (2000) Nat. Biotechnol. 18: 455-457). Genetic variants of soybeans can also be obtained, for example, by oligonucleotide-directed mutagenesis, linker-scanning mutagenesis, mutagenesis using the polymerase chain reaction, and the like. See, for example, Ausubel, pages 8.0.3-8.5.9..

Also, see generally, McPherson (ed.), DIRECTED MUTAGENESIS: A Practical approach, (IRL Press, 1991). Following mutagenesis, the seeds are planted, evaluated and seeds of desirable novel genetic profiles are selected that are viable and capable of subsequent use. The resulting seeds can then be processed in accordance with the invention to remove the transgenic event and the resulting novel genetic profile progeny used in breeding and development programs.

This invention relates to a plant breeding method for identifying a transgenic plant, or cells or tissues thereof, which method is based on identifying the presence or absence of at least one transgenic DNA sequence. According to one aspect of the invention, the method for identifying in progeny of a transgenic plant, or cells or tissues thereof, comprises amplifying a sequence of a nucleic acid present in biological samples, using a polymerase chain reaction, with at least two primers, one of which recognizes, or hybridizes with, the plant DNA in the 5' or 3' flanking region of an insertion event, the other which recognizes a sequence within the inserted transgenic DNA. Preferably, the genomic DNA is analyzed according to the PCR identification protocol described here whereby one primer recognizes a sequence within the respective 5' or 3' flanking region comprising the nucleotide sequence of SEQ ID NO: 1 or SEQ ID NO:2 or its complement. Alternatively, the primers used may recognize a sequence within the insert comprising the nucleotide sequence of SEQ ID NO: 3, and the primer recognizing a sequence within the 3' flanking region comprises the nucleotide sequence of SEQ ID NO:5, so that at least one specific amplified fragment is detected.

This invention also relates to a method for producing a non-transgenic elite crop variety, comprising crossing an elite line, comprising a transgene and exhibiting one or more transgenically-derived elite traits and one or more conventionally-derived elite traits or characteristics with a conventional non-transgenic line; obtaining individual F1 hybrid lines; selecting at least one F1 hybrid individual exhibiting elite characteristics of the elite line; deriving at least one further progeny generation of seeds or plants from the selected F1 hybrid individual; screening F2 or later progeny of the hybrid individual exhibiting the conventionally-derived elite traits or characteristics of the elite line for the presence of the transgene; and selecting progeny exhibiting the conventionally-derived elite traits or characteristics of the elite line wherein the transgene is absent from the progeny genome.

The invention also relates to a method for identifying null segregate for a transgene in a plant breeding program, comprising crossing a first line containing a transgene that encodes a useful trait inserted into its genome with a second line; obtaining F1 hybrid individuals; deriving at least one further progeny generation of seeds or plants from the F1 individual; performing zygosity analysis on the further progeny generation, and optionally Southern or western analyses; selecting progeny wherein elements of the transgene are absent and the insertion site of the transgene is restored to approximate its native state, and deriving further generations of the selected progeny wherein the removal of transgene is not caused by the presence of a transgenic recombined.

The present invention also relates to methods for identifying the presence or absence of DNA sequences in biological samples from progeny of a parent that comprises a transgene, the methods being based on primers or probes that specifically recognize the 5' and 3' plant DNA flanking sequence of the insert(s) of the transgenic event. Depending on the presence or absence of a transgene, an amplification product of a specific size can be detected.

The invention thus also relates to a kit for following the segregation of transgenic sequences in segregating progeny of an elite transgenic event, the kit comprising at least one primer or probe that specifically recognizes the 5' or 3' flanking region of the event, such that the presence, absence, or copy number of a given event may be followed during the plant breeding process.

Preferably the kit of the invention comprises, in addition to a primer that specifically recognizes the 5' or 3' flanking region of a given event, a second primer that specifically recognizes a sequence within the inserted DNA of the event, for use in a PCR identification protocol. Preferably, the kit of the invention comprises two (or more) specific primers, one of which recognizes a sequence within the 5' flanking region of an event, for instance a sequence within the plant DNA region of SEQ ID NO: 1 or SEQ ID NO:2, and another which recognizes a sequence within the inserted DNA. Especially preferably, the primer recognizing the plant DNA sequence within a 5' flanking region comprises the nucleotide sequence of SEQ ID NO:4, and the primer recognizing the inserted DNA comprises the nucleotide sequence of SEQ ID NO:3.

DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

DESCRIPTION OF THE SEQUENCE LISTINGS

Figure 1:
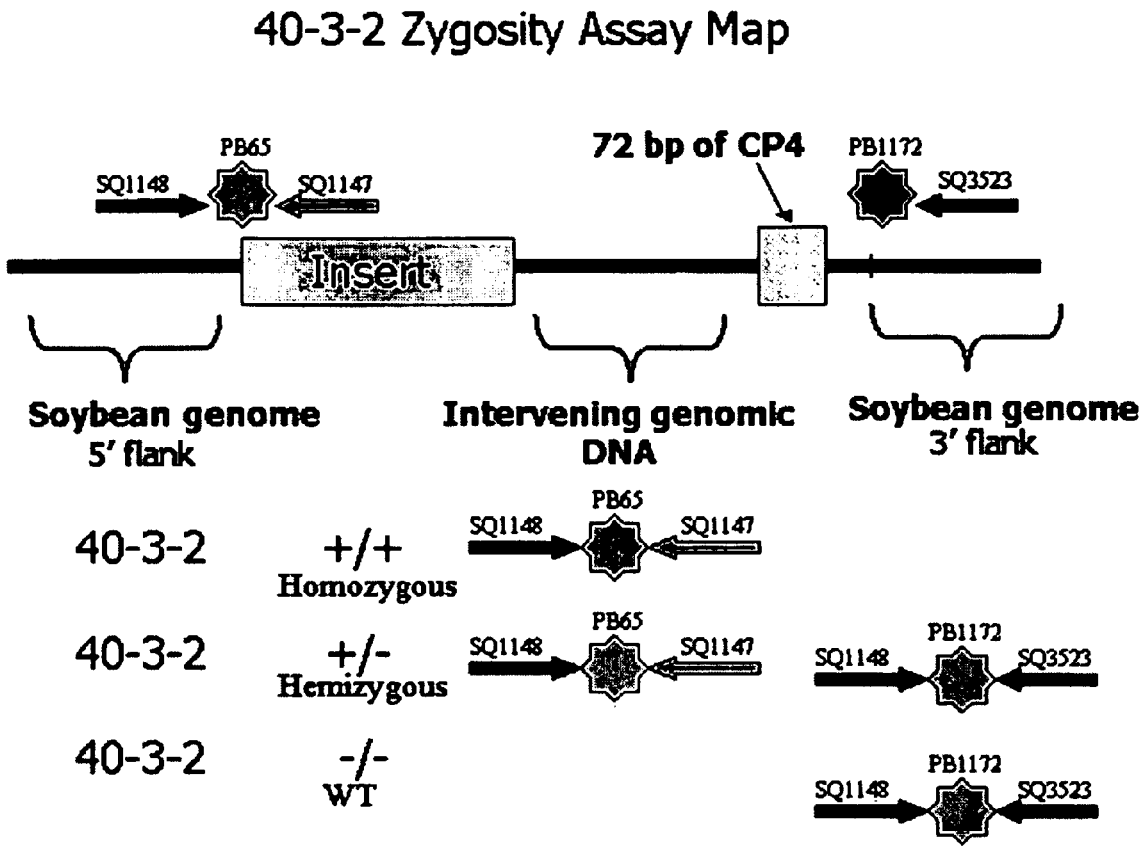
FIG. 1 is a schematic map of 40-3-2 event and amplification result.
Figure 2:
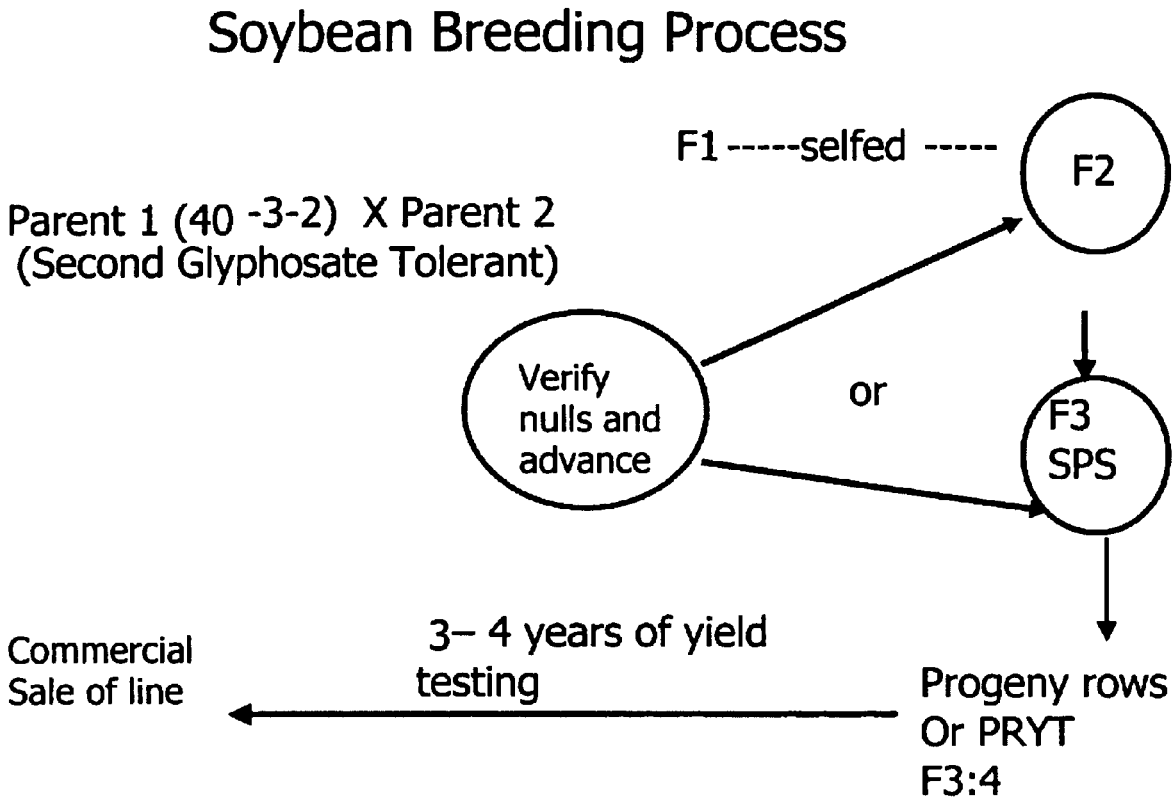
FIG. 2 illustrates a soybean breeding process.
Figure 3:
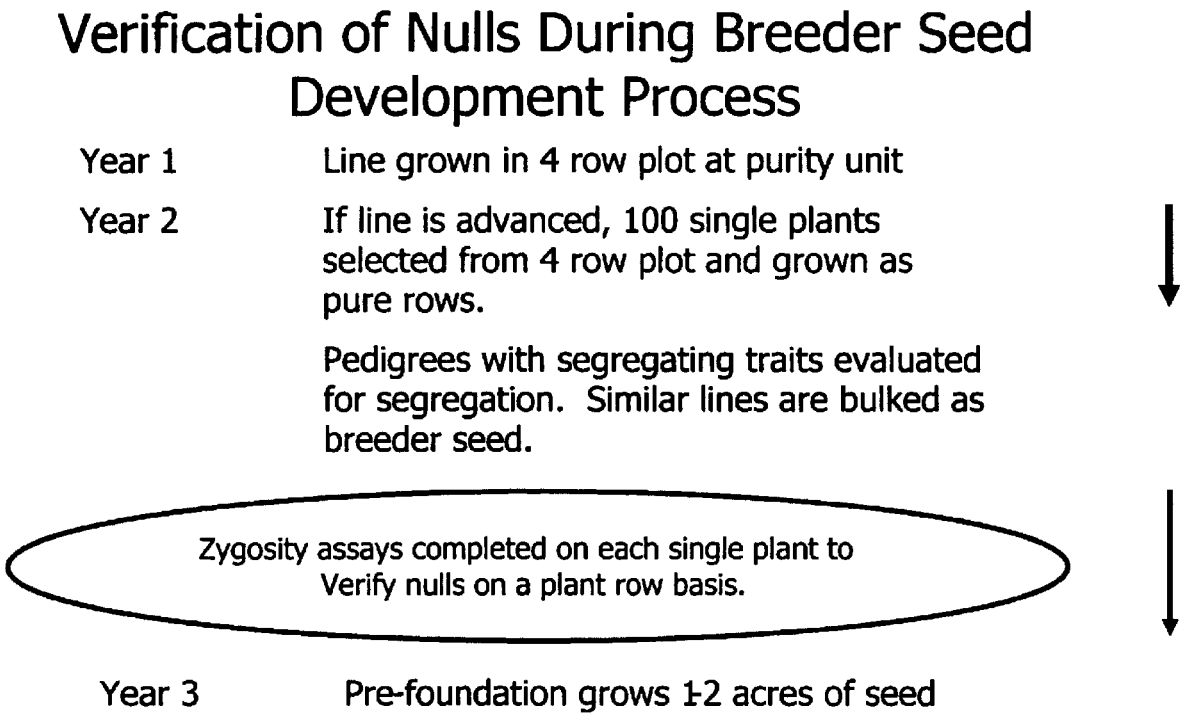
FIG. 3 provides a verification scheme of nulls.

The following sequence listings form part of the present specification and are included to further demonstrate certain aspects of the present invention. The invention may be better understood by reference to one or more of these sequences in combination with the detailed description of specific embodiments presented herein.

TABLE 1

| SEQ ID NO: | Description |
|---|---|
| 1 | 5' flanking genomic DNA and junction fragment of functional insert in 40-3-2 event |
| 2 | 3' flanking genomic DNA and junction fragment of functional insert in 40-3-2 event |
| 3 | SQ1147 primer; in transgene |
| 4 | SQ1148 primer; in 5' flanking genomic DNA |
| 5 | SQ3523 primer; in 3' flanking genomic DNA |
| 6 | PB65 fluorogenic primer; at 5' genomic-transgene junction |
| 7 | PB1172 fluorogenic primer; at 3' genomic-transgene junction |
| 8 | ract-F primer |
| 9 | ract-R primer |

DEFINITIONS

The present invention is based, in part, on preserving elite germplasm by the identification of a genomic region comprising a transgene insert in the genome of a genetically modified crop first parent elite plant and the homologous region in the genome of a second parent plant of the same species not having the identical transgene insert, and utilizing DNA molecules in a DNA detection method to select progeny plants resulting from a cross of the parent plants, wherein the selected progeny plants do not contain the specific transgene insert of the first parent plant and contain some or all of the elite germplasm characteristics of the first parent. The following descriptions are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York, (1991); and Lewin, Genes V, Oxford University Press: New York, (1994). The nomenclature for DNA bases as set forth at 37 CFR § 1.822 is used. The standard one- and three-letter nomenclature for amino acid residues is used.

"DNA segment" refers to a DNA molecule that has been isolated free of total genomic DNA of a particular species.

The term "soybean" means "Glycine max" or soybean and includes all plant varieties that can be bred with soybean, including wild soybean species.

An "elite line" can refer, for example, to a crop genotype displaying one or more molecular or agronomic or quality or industrial traits of interest.

"Glyphosate" refers to N-phosphonomethylglycine and its' salts, Glyphosate is the active ingredient of ROUNDUP® herbicide (Monsanto Co.). Plant treatments with "glyphosate" refer to treatments with the ROUNDUP® or ROUNDUP ULTRA® herbicide formulation, unless otherwise stated. Glyphosate as N-phosphonomethylglycine and its' salts (not formulated ROUNDUP® herbicide) are components of synthetic culture media used for the selection of bacteria and plant tolerance to glyphosate or used to determine enzyme resistance in in vitro biochemical assays. Examples of commercial formulations of glyphosate include, without restriction, those sold by Monsanto Company as ROUNDUP®, ROUNDUP® ULTRA, ROUNDUP® ULTRAMAX, ROUNDUP® WEATHERMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Zeneca Limited as TOUCHDOWN® herbicide, which contains glyphosate as its trimethylsulfonium salt. Glyphosate herbicide formulations can be safely used over the top of glyphosate tolerant crops to control weeds in a field at rates as low as 8ounces/acre upto 64ounces/acre. Experimentally, glyphosate has been applied to glyphosate tolerant crops at rates as low as 4ounces/acre and upto or exceeding 128ounces/acre with no substantial damage to the crop plant.

The term "probe" is an isolated nucleic acid to which is attached a conventional detectable label or reporter molecule, e.g., a radioactive isotope, ligand, photoluminescent agent, or enzyme. Such a probe is complementary to a strand of a target nucleic acid, in the case of the present invention, to a strand of genomic DNA from soybean event 40-3-2 whether from a soybean plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

The term "primer" refers to isolated nucleic acids that are annealed to a complementary target DNA stand by nucleic acid hybridization to form a hybrid between the primer and the target DNA stand, then extended along the target DNA stand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

The basis of this amplification method is multiple cycles of temperature changes to denature, then re-anneal the DNA primer molecules, followed by extension to synthesize new DNA strands in the region located between the flanking DNA primers. In general, DNA amplification can be accomplished by any of the various polynucleic acid amplification methods known in the art, including PCR. A variety of amplification methods are known in the art and are described, inter alia, in U.S. Patent Nos. 4,683,195and 4,683,202and in PCR Protocols: A Guide to Methods and Applications, ed. Innis et al., Academic Press, San Diego, 1990. PCR amplification methods have been developed to amplify up to 22kb (kilobase) of genomic DNA and up to 42kb of bacteriophage DNA (Chang et al., Proc. Natl. Acad. Sci. USA 91:5695-5699, 1994). These methods, as well as other methods known in the art of DNA amplification may be used in the practice of the present invention.

The nucleic acid probes and primers of the present invention hybridize under stringent conditions to a target DNA sequence. Hybridization refers to the ability of a strand of nucleic acid to join with a complementary strand via base pairing. Hybridization occurs when complementary sequences in the two nucleic acid strands bind to one another. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haynes et al., In: *Nucleic Acid Hybridization, A Practical Approach*, IRL Press, Washington, DC (1985), hence forth referred to as Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a "substantially homologous DNA molecule" is a polynucleic acid molecule that will specifically hybridize to the complement of the polynucleic acid to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989at 9.47-9.52, 9.56-9.58; Kanehisa, (Nucl. Acids Res. 12:203-213, 1984); and Wetmur and Davidson, (J. Mol. Biol. 31:349-370, 1988). Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively high stringent conditions to form the hybrids, e.g., one will select relatively low salt and/or high temperature conditions, such as provided by about 0.02M to about 0.15M NaCl at temperatures of about 50° C. to about 70° C. A high stringent condition, for example, is to wash the hybridization filter at least twice with high-stringency wash buffer (0.2X SSC, 0.1% SDS, 65° C). Appropriate moderate stringency conditions that promote DNA hybridization, for example, 6.0×sodium chloride/sodium citrate (SSC) at about 45° C., followed by a wash of 2.0×SSC at 50° C., are known to those skilled in the art or can be found in *Current protocols in Moloecular Biology*, John Wiley & Sons, N.Y. (1989), 6.3.1-6.3.6. Additionally, the salt concentration in the wash step can be selected from a low stringency of about 2.0×SSC at 50° C. to a high stringency of about 0.2× SSC at 50° C. Additionally, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little mismatch between the probe and the template or target strand. Detection of DNA sequences via hybridization is well known to those of skill in the art, and the teachings of U.S. Patent Nos. 4,965,188 and 5,176,995 are exemplary of the methods of hybridization analyses.

The diagnostic amplicon produced by these methods may be detected by a plurality of techniques. One such method is Genetic Bit Analysis (Nikiforov, et al. Nucleic Acid Res. 22:4167-4175, 1994) where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single- stranded PCR product can be hybridized to the immobilized oligonucleotide and serve as a template for a single base extension reaction using a DNA polymerase and labelled dideoxmucleotide triphosphates (ddNTPs) specific for the expected next base. Readout may be fluorescent or ELISA-based. A signal indicates presence of the transgene/genomic sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPS are added individually and the incorporation results in a light signal that is measured. A light signal indicates the presence of the transgene/genomic sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is desired that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/genomic sequence due to successful amplification, hybridization, and single base extension.

TAQMAN™ (PE Applied Biosystems, Foster City, CA) is descried as a method of detecting and quantifying the presence of a DNA sequence and is fully understood in the instructions provided by the manufacturer. Briefly, a FRET oligonucleotide probe is desired that overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the transgene/genomic sequence due to successful amplification and hybridization.

Molecular Beacons have been described for use in sequence detection as described in Tyangi, et al. (Nature Biotech. 14:303- 308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPS. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

ILLUSTRATIVE EMBODIMENTS OF THE INVENTION

Transgenic crops for which the method of the present invention can be applied include, but are not limited to herbicide tolerant crops, for example, ROUNDUP READY® Cotton 1445 and 88913; ROUNDUP READY® corn GA21 , NK603 , MON802 , MON809 ; ROUNDUP READY® Sugarbeet GTSB77 and H7-1 ; ROUNDUP READY® Canola RT73 and GT200 ; oilseed rape ZSR500 , ROUNDUP READY® Soybean 40 -3 -2 , ROUNDUP READY® Bentgrass ASR368 , HCN10 , HCN28 and HCN92 canola, MS1 and RF1 canola, OXY-235 canola, PHY14 , PHY35 and PHY36 canola, RM3-3 ,RM3 -4 and RM3 -6 chicory, A2704-12 , A2704 -21 , A5547 -35 , A5547 -127 soybean, GU262 soybean, W62 and W98 soybean, soybean event 781 , 19 -51 A cotton, 31807 and 31808 cotton, BXN cotton, BXN cotton, FP967 flax, LLRICE06 and LLRICE62 rice, MON71800 MON7180 wheat, 676 and 678 and 680 corn, B16 corn, Bt11 corn, CBH-351 corn, DAS-06275-8 corn, DBT418 corn, MS3 and MS6 corn, T14 and T25 corn, H177 corn, and TC1507 corn.

Herbicides for which transgenic plant tolerance has been demonstrated and the method of the present invention can be applied, include but are not limited to: glyphosate, glufosinate, sulfonylureas, imidazolinones, bromoxynil, dalapon, cyclohezanedione, protoporphyrinogen oxidase inhibitors, and isoxaflutole herbicides. Polynucleotide molecules encoding proteins involved in herbicide tolerance are known in the art, and include, but are not limited to, a polynucleotide molecule encoding 5-enolpyruvylshikimate-3-phosphate synthase (EPSPS) described in U.S. Pat. No. 5,627,061, U.S. Pat. No. 5,633,435, U.S. Pat. No. 6,040,497 and in U.S. Pat. No. 5,094,945 for glyphosate tolerance, all of which are hereby incorporated by reference; polynucleotides encoding a glyphosate oxidoreductase and a glyphosate-N-acetyl transferase (GOX, U.S. Pat. 5,463,175 and GAT, U.S. Patent publication 20030083480, herein incorporated by reference); a polynucleotide molecule encoding bromoxynil nitrilase (Bxn) described in U.S. Pat. No. 4,810,648for Bromoxynil tolerance, which is hereby incorporated by reference; a polynucleotide molecule encoding phytoene desaturase (crtI) described in Misawa et al, (1993) *Plant J.* 4:833-840and Misawa et al, (1994) *Plant J.* 6:481-489 for norflurazon tolerance; a polynucleotide molecule encoding acetohydroxyacid synapse (AHAS, aka ALS) described in Sathasiivan et al. (1990) *Nucl. Acids Res.* 18:2188-2193 for tolerance to sulfonylurea herbicides; and the bar gene described in DeBlock, et al. (1987) *EMBO J.* 6:2513- 2519 for glufosinate and bialaphos tolerance; resistant hydroxyphenyl private dehydrogenase HPPD, U.S. Pat. No. 6,768,044). The promoter of the present invention can express genes that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, glyphosate oxidoreductase and glyphosate-N-acetyl transferase.

Transgenic crops for which the method of the present invention can be applied to include, but are not limited to, insect resistant crops, for example, cotton events, such as MON15985, 281-24-236, 3006-210-23, MON531, MON757, MON1076, and COT102; or corn events, such as 176, BT11, CBH-351, DAS-06275-8, DBT418, MON80100, MON810, MON863, TC1507, MIR152V, 3210M, and 3243M.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should in light of the present disclosure, appreciate that many changes can be made in the specific embodiments which are disclosed and still obtain a like or similar result without departing from the spirit and scope of the invention.

EXAMPLES

Example 1: Progeny of 40-3-2 lacking inserted DNA

An elite soybean cultivar comprising ROUNDUP READY® event 40-3-2 is crossed with a conventional (non-transgenic) cultivar, and segregation of traits and the transgene is followed by PCR zygosity testing. The presence of 5' or 3' junction sequences may be followed as shown schematically in FIG. 1. The PCR assay may be either singleplex, or multiplex. An internal quantitation control may be included. In the case of the 40-3-2 event, the inserted DNA consists of, in the 5' to 3' direction, a functional insert, an intervening (rearranged) genomic DNA, a non-functional 72 bp fragment of the gene encoding CP4 EPSPS, and additional genomic sequence. Referring to FIG. 1, use of primer set A-B-C on template DNA derived from progeny of a cross of soybean event 40-3-2 with another plant, for instance, allows one to positively differentiate between progeny that are homozygous for the inserted DNA, homozygous for the inserted DNA, or lack the inserted DNA. PCR primer design based on known DNA sequences is well known in the art. Exemplary primers in this example include SEQ ID NO:3 (primer B), SEQ ID NO:4 (primer A), and SEQ ID NO:5 (primer C).

Template DNA is extracted from plant leaf tissues or round seed from progeny of the cross noted above. Briefly, a 7-mm hole punch may be used to harvest tissue of a newly formed leaf of a young plant (less than 1 month old). The tissue is lyophilized and stored in a tube until needed. Three 3 mm glass beads are added to the tissue, and the tube is agitated to grind the tissue into a fine powder. 600 μl of extraction buffer (100 mM Tris; 1 mM KCl; 10 mM EDTA; pH 9.5) is added and after the tube is agitated to resuspend the powdered tissue it is incubated at 65° C. for 1 hour, followed by centrifugation for 1 minute at 1500 RPM. 200 μl of precipitation buffer (5 M KAc; pH 7.0) is added and the tube is agitated to thoroughly mix, followed by centrifugation at 3000 RPM for 10 minutes. 600 μl of supernatant containing DNA is transferred to a new tube containing 500 μl isopropanol, mixed, and left at room temperature for 10 minutes. The tube is centrifuged for 5 minutes at 3000 RPM to pellet the DNA and supernatant is removed. The DNA pellet is dried at 65° C. for 30 minutes, and then 200 μl of TE (10 mM Tris; 1 mM EDTA) buffer is added and incubated at room temperature for at least 30 minutes. The pellet is agitated for 1 minute, centrifuged for 1 minute at 1000 RPM, and stored at 4° C.

Following template DNA extraction, TAQMAN™ PCR multiplex amplification reaction is performed on each sample. 3 μl of extracted template DNA is mixed with 0.2 μl WT VIC™ internal control probe [SEQ ID NO:7] suspended in 18 megohm purified water [Sigma Catalog No. W-4502] (0.2 μM final concentration); 0.2 μl Event 6-FAM™ MGB probe [SEQ ID NO:6] suspended in 18 megohm purified water (0.2 μM final concentration); 0.5 μl of zygosity probe primer mix suspended in 18 megohm purified water (1.0 μM final concentration prepared by suspending each primer [SEQ ID NO:3, SEQ ID NO:4, and SEQ ID NO:5] in 18 megohm water at a concentration of 20 μM; and 5 μl of 2X universal master buffer mix [Applied Biosystems part No. 4304437]. Final volume is adjusted to 10 μl with 18 megohm water, and PCR is performed in an Applied Biosystems GeneAmp PCR System 9700 or an MJ Research DNA Engine PTC-225 thermal cycler by using the following parameters; 1 cycle 50° C., 2 minutes; 1 cycle 95° C., 10 minutes; 10 cycles of 95° C., 15 seconds, followed by 64° C., 1 minute, −1° C./cycle; 30 cycles of 95° C., 15 seconds, followed by 54° C., 1 minute; and 1 cycle of 10° C., hold temperature.

The following positive controls are used: template DNA from known homozygous 40-3-2 transgenic soybean; template DNA from known hemizygous 40-3-2 transgenic soybean. The following negative controls are used: template DNA from known non-transgenic soybean; no template DNA control.

FAM probe fluorescence is read at 520 nM; VIC™ probe fluorescence is read at 550 nM. Fluorogenic MGB TAQMAN™ probes are PB65 (6FAM-CCTTTTCCATTTGGG; SEQ ID NO:6) and PB1172 (VIC™-ACCTCGTTTCTATGCTAATTAC; SEQ ID NO:7).

Following crossing of a 40-3-2 line with a conventional line, progeny lines are identified that lack a detectable amplified insert sequence, and are screened for glyphosate sensitivity and traits of interest. Marker-assisted breeding may be employed in this process. The presence of a transgene may also be assessed in progeny by means of other methods such as other PCR-based methods, Southern blots, northern blots, western blots, or ELISA analysis.

Example 2: Trangenic progeny of 40-3-2 that comprose a different glyphosate tolerance transgene, and do not contain the functional 40-3-2 insertion An elite soybean cultivar comprising ROUNDUP READY® event 40-3-2 may be crossed with a soybean cultivar comprising a different transgenic event that confers glyphosate tolerance, and segregation of the two transgenic inserts and additional agronomic traits is followed. The PCR-based zygosity test for sequences specific to event 40-3-2 is performed as described in Example 1. Similar zygosity testing may optionally be performed to identify progeny homozygous or hemizygous for the other transgenic event or events. Progeny are screened by the PCR-based zygosity test for loss of the 40-3-2 insertion, and selected for glyphosate resistance and other traits of interest.

The methods used to identify heterozygous from homozygous progeny containing 40-3-2 insertion DNA are described in a zygosity assay for which examples of conditions are described in Table 2 and Table 3. The DNA primers used in the zygosity assay are primers (SEQ ID NO:3), (SEQ ID NO:4), (SEQ ID NO:5), 6FAM™ labeled primer (SEQ ID NO:6) and VIC™ labeled primer (SEQ ID NO:7), 6FAM and VIC are florescent dye products of Applied Biosystems (Foster City, Calif.) attached to the DNA primer.

SEQ ID NO:3, SEQ ID NO:4 and SEQ ID NO:5 when used in these reaction methods produce one DNA amplicon for non-transgenic soybean, two DNA amplicons for heterozygous soybean containing event 40-3-2 DNA, and one DNA amplicon for homozygous 40-3-2 soybean plant. The controls for this analysis should include a positive control from homozygous and heterozygous soybean containing event 40-3-2 DNA, a negative control from non-transgenic soybean, and a negative control that contains no template DNA. This assay is optimized for use with a Stratagene Robocycler, MJ Engine, Perkin-Elmer 9700, or Eppendorf Mastercycler Gradient thermocycler. Other methods and apparatus known to those skilled in the art that produce amplicons that identify the zygosity of the progeny of crosses made with 40-3-2 plants is within the skill of the art.

TABLE 2

Zygosity assay reaction solutions

| Step | Reagent | Amount | Comments |
|---|---|---|---|
| 1 | Nuclease-free water | add to 10 μl final volume | — |
| 2 | 2X Universal Master Mix (Applied Biosystems cat. # 4304437) | 5 μl | 1 X final concentration |
| 3 | Primers SEQ ID NO: 3, 4, and 5 (resuspended in nuclease-free water to a concentration of 20 μM) | 0.5 μl | 0.25 μM final concentration |
| 4 | Primer 6FAM ™ (resuspended in nuclease-free water to a concentration of 10 μM) | 0.2 μl | 0.4 μM final concentration |
| 5 | Primer VIC ™ (resuspended in nuclease-free water to a concentration of 10 μM) | 0.2 μl | 0.15 μM final concentration |
| 6 | REDTaq DNA polymerase (1 unit/μl) | 1.0 μl (recommended to switch pipets prior to next step) | 1 unit/reaction |
| 7 | Extracted DNA (template): | 3.0 μl | Diluted in water |
| | Samples to be analyzed (individual leaves) | 4-80 ng of genomic DNA | |
| | Negative control | 4 ng of non-transgenic soybean genomic DNA | |
| | Negative control | no DNA template (solution in which DNA was resuspended) | |
| | Positive control | 4 ng of genomic DNA from known event 40-3-2 heterozygous soybean | |
| | Positive control | 4 ng of genomic DNA from known event 40-3-2 homozygous soybean | |
| 8 | Gently mix, add 1-2 drops of mineral oil on top of each reaction. | | |

Zygosity assay thermocycler conditions: Proceed with the DNA amplification in a Stratagene Robocycler, MJ Engine, Perkin-Elmer 9700, or Eppendorf Mastercycles Gradient thermocycler using the following cycling parameters. When running the PCR in the Eppendorf Mastercycler Gradient or MJ Engine, the thermocycler should be run in the calculated mode. When running the PCR in the Perkin-Elmer 9700, run the thermocycler with the ramp speed set at maximum.

TABLE 3

| Cycle No. | | |
|---|---|---|
| | Settings: Stratagene Robocycler | |
| 1 | 94° C. | 3 minutes |
| 38 | 94° C. | 1 minute |
| | 60° C. | 1 minute |
| | 72° C. | 1 minute and 30 seconds |
| 1 | 72° C. | 10 minutes |
| | Settings: MJ Engine or Perkin-Elmer 9700 | |
| 1 | 94° C. | 3 minutes |
| 38 | 94° C. | 30 seconds |
| | 60° C. | 30 seconds |
| | 72° C. | 1 minute and 30 seconds |
| 1 | 72° C. | 10 minutes |
| | Settings: Eppendorf Mastercycler Gradient | |
| 1 | 94° C. | 3 minutes |
| 38 | 94° C. | 15 seconds |
| | 60° C. | 15 seconds |
| | 72° C. | 1 minute and 30 seconds |
| 1 | 72° C. | 10 minutes |

Example 3: Conversion of a GA21 event-containing corn line - segregant analysis The present invention may be applied to corn breeding. An inbred corn line comprising event GA21 was crossed to another inbred line comprising event NK603, and segregation of progeny was followed in order to efficiently identify progeny that lack sequences associated with the GA21 event, comprise the NK603 event, and exhibit other DNA markers of the original parent line that comprises GA21.

Conversion of the GA21 line was performed by means of a multi-tiered marker-assisted breeding approach of event-specific PCR-based assays, linked-marker PCR and Southern blot analysis, to confirm the presence of event NK603-related DNA sequences and absence of event GA21-related DNA sequences. Following multiple backcrosses, we confirmed the presence of the NK603 event, and of DNA markers associated with the genetic background and agronomic qualities of the original parent that comprises GA21.

The recurrent parent corn inbred line RR728-18GA21 was crossed with donor parent 9034(5)NK603, and backcrossed to the recurrent parent. The BC1S0 was crossed to the recurrent parent, and its genotype was screened by PCR-based assay. Lines exhibiting probable heterozygosity at both transgenic loci were selected and ranked according to the number of PCR markers present for the recurrent parent (RP). Selected lines (BC2S0 generation) were backcrossed to the recurrent parent again (BC3S0), selfed, and screened by Taqman PCR. Of 558 lines sampled, 165 comprised the NK603 event, and 38 of those 165 were deemed highly probable as being heterozygous for GA21 based on the GA21 event assay and co-dominant linked marked. This generation was selfed to yield a BC3F2 generation, and progeny were again screened with respect to GA21-linked PCR markers, NK603 PCR-based zygosity assay, and percentage of recurrent parent markers (PCR-based). Lines selected for further breeding at this stage comprised up to almost 95% recurrent parent markers, were heterozygous for GA21, and comprised NK603 (table 4).

TABLE 4

| Line | % Recurrent Parent Markers |
|---|---|
| 304 | 90.89 |
| 312 | 89.78 |
| 323 | 91.94 |
| 336 | 94.94 |
| 397 | 90.72 |
| 406 | 92.77 |

The BC3F2 generation was selfed, and progeny were grown and selected for tolerance to ROUNDUP®; marker-assisted selection for presence of homozygous null GA21 and homozygous NK603, and highest percentage of recurrent parent markers. 15 out of 251 screened lines were homozygous null GA21 (i.e. lack the GA21 event) and homozygous for the NK603 event. Sixty pools of 5 progeny each of selected lines were subjected to Southern blot analysis of EcoRV-digested genomic DNA. Control lanes included genomic DNA from known GA21 and NK603 corn lines, and a sample of GA21 genomic DNA spiked 1:9 into NK603 genomic DNA to stimulate the presence of hemizygous GA21-containing plant in a five plant pool.

A rice actin promoter probe was used. The probe was prepared by PCR synthesis using pDPG434 as template DNA, and primers ract-F TCGAGGTCATTCATATGCTTGAGAAG [SEQ ID NO:8] and ract-R AAGCTCCGCACGAGGCTGCATTTG [SEQ ID NO:9] followed by digoxigenin labeling. pDPG434 is the plasmid construct used to give rise to the GA21 event (U.S. Pat. No. 6,040,497, incorporated herein by reference), and contains elements in common with the plasmid construct used to give rise to the NK603 event. The probe is a 1.4 Kb DNA fragment spanning the rice actin1 promoter, intron, and 5' untranslated region (UTR). With this probe, NK603-containing genomic DNA yields a hybridizing band of 4 Kb, and GA21- containing genomic DNA yields a hybridizing band of about 21 Kb. The resulting hybridization pattern indicated detectable NK603-specific signal and no detectable GA21-specific signal in experimental lanes. Control lanes yielded expected size GA21 and NK603 specific signals, confirming that the assay was sensitive enough to identify a single hemizygous GA21 individual in a pool of five plants. The converted inbred line is identified as 9034 (NK603).

This method may also be used to identify non-transgenic progeny (i.e. null segregate for both transgenic events) in a cross such as that described above. Such null segregate would, in this case, comprise neither the GA21 nor NK603 events, but may comprise genetic markers and agronomic qualities of either or both parent lines.

All of the methods disclosed and claimed herein can be made and executed without undue experimentation in light of the present disclosure. While the methods of this invention have been described in terms of preferred embodiments, it will be apparent to those of skill in the art that variations may be applied in the steps or in the sequence of steps of the methods described herein without departing from the concept, spirit and scope of the invention. All such similar substitutes and modifications apparent to those skilled in the art are deemed to be within the spirit, scope and concept of the invention.

REFERENCES

The following references, to the extent that they provide exemplary procedural or other details supplementary to those set forth herein, are specifically incorporated herein by reference:

U.S. Pat. Nos. 6,825,400; 6,818,807; 6,468,747; 6,563,026; 6,040,497

Hare & Chua *Nature Biotechnol.* 20:575-580

Padgette, *Crop Sci.* 35:1451-1461

Windels, *Eur Food Res. Technol.* 213:107-112

Bubner, *BMC Biotechnol.* 4:14 (2004)

Schmidt, *Plant Cell Rep.* 20:422-428

Song, *Plant Cell Rep.* 20:948-954

Bubner, *Plant Cell Rep.* 23:263-271

Windels, *Med. Fac. Landbouww Univ. Gent.* 64/5b:459-462

Fehr, W. R. 1987. *Principles of Cultivar Development Vol. 1: Theory and Technique.*

Simmonds, N. W. and J. Smartt. 1999. Principles of Crop Improvement. 2nd Ed.

SEQUENCE LISTING

```
<160> NUMBER OF SEQ ID NOS: 9

<210> SEQ ID NO 1
<211> LENGTH: 291
<212> TYPE: DNA
<213> ORGANISM: Unknown
<220> FEATURE:
<223> OTHER INFORMATION: Junction of 5' end of insert with soybean
      sequence

<400> SEQUENCE: 1

cgtgggtggg gtccatcttt gggaccctgt cggcagaggc atcttcaacg atggcctttc      60

ctttatcgca atgatggcat ttgtaggagc caccttcctt ttccatttgg gttccctatg     120

tttattttaa cctgtatgta tgatcttatt ttgaatgaaa tgcaataagt tatttctagt     180

aaaaaaaaat aaacatttga tagaaacaaa ttaaagcatg caaaaataac tcattagcat     240

cggttaaatt gaagggtttg aataatttgc acaaggttct gaattcaaat c              291
```

-continued

<210> SEQ ID NO 2
<211> LENGTH: 860
<212> TYPE: DNA
<213> ORGANISM: Unknown
<220> FEATURE:
<223> OTHER INFORMATION: Junction of 3' end of insert with soybean
sequence

<400> SEQUENCE: 2 tttctgttga atacgttaag catgtaataa ttaacatgta atgcatgacg ttatttatga 60 gatgggtttt tatgattaga gtcccgcaat tatacattta atacgcgata gaaaacaaaa 120 tatagccgcg caaactagga taaattatcg cgcgcggtgt catctatgtt actagatcgg 180 ggatcgatcc cccaccggtc cttcatgttc ggcggtctcg cgagcggtga aacgcgcatc 240 accggccttc tggaaggcga ggacgtcatc aatacgggca aggccatgca ggccatgggc 300 gccaggatcc gtaaggaagg cgacacctgg atcatcgatg gcgtcggcaa tggcggcctc 360 ctggcgcctg aggcgccgct cgatttcggc aatgccgcca cgggctgccg cctgaccatg 420 ggcctcgtcg gggtctacga tttcaagcgc atcatgctgg gaaattttag cgagattata 480 agtatcttcc tggggatctc tgctgttact ggtgaatagt gagacagagt cttctgagct 540 cataggataa aataaattat aattagtaaa ttttttaatt aaataaatca attacttcat 600 aaataatttt ttttatagaa tatgttgaca ttctagctgg atatagaact aatataaaga 660 aaccttaaaa attttgtttg gaagaatatg ttattgaaag acaaatctaa ttaagtttat 720 cagggtcatt tgttgaagat aggaaacctt cagcaatttg aatattaagt aactgcttct 780 cccagaatga tcggagtttc tcctcctgct attacatgaa aaaaaataaa aaataaaaaa 840 aagataagat taagcttcaa 860

<210> SEQ ID NO 3
<211> LENGTH: 21
<212> TYPE: DNA
<213> ORGANISM: Artificial sequence
<220> FEATURE:
<223> OTHER INFORMATION: Primer SQ1147

<400> SEQUENCE: 3 ggcatttgta ggagccacct t 21

<210> SEQ ID NO 4
<211> LENGTH: 31
<212> TYPE: DNA
<213> ORGANISM: Artificial sequence
<220> FEATURE:
<223> OTHER INFORMATION: Primer SQ1148

<400> SEQUENCE: 4 ttcattcaaa ataagatcat acatacaggt t 31

<210> SEQ ID NO 5
<211> LENGTH: 23
<212> TYPE: DNA
<213> ORGANISM: Artificial sequence
<220> FEATURE:
<223> OTHER INFORMATION: Primer SQ3523

<400> SEQUENCE: 5 gtgtcgttca catctttgca aga 23

<210> SEQ ID NO 6

-continued

```
<211> LENGTH: 15
<212> TYPE: DNA
<213> ORGANISM: Artificial sequence
<220> FEATURE:
<223> OTHER INFORMATION: FAM TaqMan probe PB65

<400> SEQUENCE: 6

ccttttccat ttggg                                                    15


<210> SEQ ID NO 7
<211> LENGTH: 21
<212> TYPE: DNA
<213> ORGANISM: Artificial sequence
<220> FEATURE:
<223> OTHER INFORMATION: VIC Taqman Probe PB1172

<400> SEQUENCE: 7

acctcgtttc tagctaatta c                                             21


<210> SEQ ID NO 8
<211> LENGTH: 30
<212> TYPE: DNA
<213> ORGANISM: Artificial sequence
<220> FEATURE:
<223> OTHER INFORMATION: Ract-F primer

<400> SEQUENCE: 8

tcgaggtcat tcattcatat gcttgagaag                                    30


<210> SEQ ID NO 9
<211> LENGTH: 24
<212> TYPE: DNA
<213> ORGANISM: Artificial sequence
<220> FEATURE:
<223> OTHER INFORMATION: Ract-R primer

<400> SEQUENCE: 9

aagctccgca cgaggctgca tttg                                          24
```

What is claimed is:

1. A method for developing an elite crop variety, comprising:

a) crossing a first elite line comprising a transgene that encodes a useful trait in said first elite line, and thatexhibits at least one elite trait, with a second line that exhibits an elite trait;

b) obtaining multiple progeny from the cross;

c) selecting at least one individual from said multiple progeny that exhibits said elite trait derived from the first elite line or second line;

d) producing at least one further progeny population from the selected individual;

e) screening said further progeny population for said one of the additional elite trait of the first elite line and for the presence of the transgene;

f) identifying at least one individual from said further progeny population that lacks the transgene of the first elite line; and (g) using the individual identified in step (f) to produce at least one additional progeny population.

2. The method of claim 1 wherein the screening process of step (e) comprises a zygosity assay or ELISA assay.

3. The method of claim 1 wherein the individual identified in step (f) further comprises the elite trait of the second line.

4. The method of claim 1 wherein the useful trait of the first elite line or the elite trait of the second line is herbicide tolerance.

5. The method of claim 4 wherein the herbicide tolerance is glyphosate tolerance.

6. The method of claim 5 wherein the glyphosate tolerance is provided by expression of glyphosate tolerant (CP4 EPSPS (5-enolpyruvylshikimate-3-phosphate synthase), EPSPS, GOX (glyphosate oxidoreductase), or GAT (glyphosate-N-acetyl transferase).

7. The method of claim 4 wherein the useful trait of the first elite line and the elite trait of thesecond line both comprise herbicide tolerance.

8. The method of claim 1 wherein the crop is selected from the group consisting of soybean, corn, cotton, rice, wheat, canola, alfalfas turfgrass, flax, sugar beet, potato, and chicory.

9. The method of claim 8, wherein the crop is soybean and the first elite line comprises glyphosate tolerant soybean event 40-3-2.

10. The method of claim 8, wherein the crop is corn and the first elite line comprises event GA21.

11. The method of claim 1, wherein the second line comprises a transgene.

12. The method of claim 1, wherein said identified individual is crossed with a glyphosate tolerant plant to produce said additional progeny population, and wherein the method further comprises:

h) selecting from said additional progeny population at least one individual plant that exhibits glyphosate tolerance;

i) deriving at least one further generation from the individual selected in step (h);

j) screening the further generation for the presence of the at least one additional elite trait of the first elite line and for glyphosate tolerance; and k) selecting at least one individual from the generation screened in step (j) that exhibits glyphosate tolerance.

13. The method of claim 12, wherein the glyphosate tolerance is provided by expression of a CP4 EPSPS, EPSPS, GOX, or GAT.

14. The method of claim 12, wherein the crop is soybean and the glyphosate tolerant plant is soybean event 781.

15. A method for producing an elite crop variety, comprising:

a) crossing an elite line that (i) comprises a transgene encoding a useful trait in said elite line and (ii) exhibits one or more transgenically- derived elite traits and one or more conventionally-derived elite traits, with a conventional non-transgenic line;

b) obtaining individual F1 hybrid lines;

c) selecting at least one F1 hybrid individual exhibiting at least one elite characteristic of the elite line;

d) deriving at least one further progeny generation from the selected F1 hybrid individual;

e) screening F2 or later progeny exhibiting at least one of the conventionally-derived elite traits of the elite line for the presence of said transgene;

f) selecting at least one individual from the progeny screened in step (e) that lacks DNA sequences of said transgene in its genome; and g) using the individual selected in step (f) to produce at least one additional progeny population.

16. The method of claim 15, wherein the elite line comprises soybean event 40-3-2.

17. The method of claim 16, wherein the elite line comprising soybean event 40-3-2 has been exposed to a mutagenizing agent to develop a unique genetic profile.

18. The method of claim 15, wherein the elite line exhibits one or more traits selected from the group consisting of: herbicide tolerance, insect resistance, and male sterility.

19. The method of claim 15, further comprising:

h) selecting from said additional progeny population at least one individual plant that exhibits one or more elite traits derived from either of its parents;

i) deriving at least one further generation from the individual selected in step (h);

j) screening the further generation for the presence of elite traits; and k) selecting at least one individual from the generation screened in step (j) that exhibits one or more elite traits.

20. A method for producing null segregants for a transgene in a plant breeding program, comprising:

a) crossing a first line containing a transgene that encodes a useful trait in said first line with a second line;

b) obtaining one or more F1 hybrid individuals;

c) deriving at least one further progeny generation from the one or more F1 individuals;

d) screening the further progeny generation for the presence of the transgene;

e) selecting progeny that do not have the transgene; and f) deriving at least one further generation from the progeny selected in step (e).

21. The method of claim 20, wherein the transgene encodes herbicide tolerant.

22. The method of claim 21, wherein the transgene encodes glyphosate tolerance.

23. The method of claim 22, wherein the transgene encodes CP4 EPSPS, EPSPS, GOX, or GAT.

24. The method of claim 20, wherein the transgene encodes an insecticidal toxin derive from *Bacilli thuringiensis*.

25. The method of claim 23, wherein the transgene encoding CP4 EPSPS comprises a plant DNA virus promoter; a sequence encoding a chloroplast transit peptide, a sequence encoding a CP4 EPSPS; and a NOS terminator.

26. The method of claim 20, wherein screening step (d) comprises performing zygosity analysis.

27. The method of claim 26, wherein screening step (d) further comprises performing Southern blot analysis or western blot analysis.

28. The method of claim 20, wherein the removal of the transgene is not caused by the presence of a transgenic recombinase.

29. The method of claim 20, wherein the method further comprises selecting at least one F1 hybrid individual obtained in step (b) that exhibits at least one characteristic of the first line.

30. The method of claim 11, wherein the individual identified in step (f) comprises the transgene of the second line.

* * * * *